United States Patent [19]

Dumas et al.

[11] Patent Number: 5,069,828

[45] Date of Patent: Dec. 3, 1991

[54] PROCESS FOR PREPARING BENZENESULFONATE SALTS

[75] Inventors: Donald J. Dumas; Vinayakam Subramanyam, both of Wilmington, Del.

[73] Assignee: E. I. Du Pont de Nemours and Company, Wilmington, Del.

[21] Appl. No.: 359,902

[22] Filed: Jun. 6, 1989

[51] Int. Cl.$^5$ .......................................... C07C 303/32
[52] U.S. Cl. ...................... 260/402; 560/14; 560/18; 560/98; 562/56
[58] Field of Search ............... 562/56; 560/14, 17, 560/18, 98; 260/402

[56] References Cited

U.S. PATENT DOCUMENTS 4,536,314 8/1985 Hardy et al. .................. 260/402
4,704,236 11/1987 Sankey et al. ................. 260/402

FOREIGN PATENT DOCUMENTS 0148148 7/1985 European Pat. Off. .
0164786 12/1985 European Pat. Off. .

Primary Examiner—Jose G. Dees
Assistant Examiner—Deborah D. Carr
Attorney, Agent, or Firm—Charles E. Krukiel

[57] ABSTRACT

An improved process for preparing benzenesulfonate salts, such as 4-nonanoyloxybenzenesulfonic acid, sodium salt, from an appropriately substituted acid chloride or chloroformate and a hydroxybenzenesulfonic acid in which the reaction is conducted in the presence of a phase transfer catalyst selected from quaternary ammonium and quaternary phosphonium salts.

9 Claims, No Drawings

PROCESS FOR PREPARING BENZENESULFONATE SALTS

BACKGROUND OF THE INVENTION

The present invention relates to an improved process for preparing benzenesulfonate salts of the formula (I)

$$RCO_2PhSO_3M \quad (I)$$

from acid chlorides or chloroformates and salts of phenolsulfonic acids in which the reaction is conducted in the presence of a phase transfer catalyst.

U.S. Pat. No. 4,704,236 describes a process for preparing acyloxybenzene sulfonate salts in which an alkali metal phenol sulfonate is reacted with an aliphatic acyl halide at a temperature of from 135° to 180° C. in the presence of an organic solvent. Alkali metal acyloxybenzene sulfonate salts precipitate from the reaction mixture as separable solids. It is stated that the aliphatic acyl halide is preferably a linear aliphatic acyl chloride which contains from 6 to 15 carbon atoms, including specifically the acid chlorides derived from heptanoic acid, octanoic acid, nonanoic acid, and decanoic acid. Where branched chain acyl chlorides are used, no difference in yield is noted whether the solvent is aromatic or aliphatic. However, when linear acyl chlorides are used, it is stated in col. 3., lines 7–13, that a very distinct benefit in yield can be achieved when the reaction is carried out in the presence of an aliphatic hydrocarbon solvent. The mole ratio of acyl chloride to alkali metal phenol sulfonate in the examples varies from about 1.5:1 to 2:1.

European Patent Application 0 148 148 describes a process for preparing sodium alkanoyloxyhalidebenzene sulfonates by reacting substantially solid anhydrous sodium phenol sulfonate with alkanoylhalide at a temperature in the range of 90° to 200° C. in the substantial absence of a solvent or an inert reaction medium.

European Patent Application 0 164 786 describes a process for preparing p-isononanoyloxybenzenesulfonate by reacting isononanoic acid chloride with potassium p-phenolsulfonate in the presence of a solvent, preferably an aromatic hydrocarbon, at a temperature in the range of 80° to 200° C.

U.S. Pat. No. 4,536,314 describes the preparation of branched chain aliphatic peroxyacid bleach precursors, such as, for example, sodium 3,5,5-trimethyl hexanoyloxybenzene sulfonate, which is obtained from the reaction of isononanoyl chloride and anhydrous sodium phenol sulfonate. Example 1 describes the reaction in greater detail. Tetrabutylammonium bromide is added to the reaction mixture as a catalyst, but there is no teaching or explanation as to the need or the desirability for employing a catalyst for this type of reaction. Moreover, the applicability of a catalyst in preparing other than branched chain, i.e., linear, precursors as well as its chemistry are left open to speculation.

Many of the compounds which can be prepared by the process of the present invention are known in the art, especially for their utility as bleach activators. The term "bleach activator" is understood in the art to describe a relatively stable compound which will decompose in water in the presence of a peroxygen to give the corresponding peracid bleaching agent.

The bleach activators which can be prepared by the process of the present invention are described in the references cited above as well as in U.K. Patent Specification No. 864,798, European Patent Application 267,048, European Patent Application 284,292, U.S. Pat. Nos. 4,483,778, 4,536,314, 4,634,551, 4,681,592, 4,778,618 and 4,735,740.

SUMMARY OF THE INVENTION

The present invention provides an improved process for preparing alkanoyloxybenzenesulfonate salts of the formula (I)

$$RCO_2PhSO_3M \quad (I)$$

where:

R is $C_1-C_{20}$ linear alkyl; $C_1-C_{15}$ alkyl substituted by $N(R_1)COR_2$, $CONR_1R_2$, $CO_2R_3$, $OR_3$ or $SO_2R_3$; $OR_3$; $CH=CHCO_2R_3$; phenyl substituted by $CO_2R_3$; $CH(OR_3)_2$; $CH(SO_2R_3)_2$; $C(R_4)(R_5)Cl$; $C(R_7)_2OC(O)R_6$; or $CH_2OR_8$;

$R_1$ is H or $C_1-C_{10}$ alkyl, aryl or alkaryl;

$R_2$ is $C_1-C_{14}$ alkyl, aryl or alkaryl;

$R_3$ is $C_1-C_{20}$ alkyl, alkenyl, alkynyl or alkaryl, optionally alkoxylated with one or more ethyleneoxy or propyleneoxy groups or mixtures thereof;

$R_4$ is $C_4-C_{14}$ alkyl or alkenyl;

$R_5$ is H, methyl or ethyl;

$R_6$ is $C_1-C_{20}$ linear or branched alkyl, alkylethoxyalkylated, cycloalkyl, aryl or substituted aryl;

$R_7$ are independently H, $C_1-C_{20}$ alkyl, aryl, $C_1-C_{20}$ alkylaryl and substituted aryl;

$R_8$ is aryl optionally substituted by $C_1-C_5$ alkyl; and

M is selected from an alkali metal or an alkaline earth metal.

Compounds within this group which are of particular utility as bleach activators, and those for which the process of the invention is particularly applicable, include the compounds where:

R is $C_5-C_9$ linear alkyl; $C_1-C_4$ alkyl substituted by $N(R_1)COR_2$, $CONR_1R_2$, $CO_2R_3$, $OR_3$ or $SO_2R_3$; $OR_3$; $C(R_7)_2OC(O)R_6$; or $CH_2OR_8$.

The alkanoyloxybenzenesulfonate salts of formula (I) are prepared by reacting an acid chloride or chloroformate (II) with the appropriate salt of phenol sulfonic acid (III) in an aprotic solvent, the improvement comprising conducting the reaction in the presence of a phase transfer catalyst (PTC) as shown in Equation 1.

Equation 1:

$$RCOCl + HOPhSO_3M \xrightarrow[\text{solvent}]{\text{PTC}} (I)$$

(II)     (III)

According to the invention, it has unexpectedly been found that the rate of reaction according to Equation 1 can be accelerated by the addition of a phase transfer catalyst selected from quaternary ammonium and quaternary phosphonium salts, in an amount ranging from 0.1 up to 10 mole percent relative to the phenol derivative (III) employed in the reaction. The process of this invention allows the preparation of alkanoyloxybenzenesulfonate salts of high purity. In addition, the process uses lower temperatures than currently known for similar processes, and the loadings of acid chloride required to carry out the reaction are lower, which, in combination, renders the process very economical.

DETAILED DESCRIPTION OF THE INVENTION

The benzenesulfonate salts of formula (I) can be prepared by reacting an acid chloride or chloroformate (II) with a salt of phenol sulfonic acid (III). Acid halides, chloroformates and phenol sulfonic acid salts suitable for use in the process of this invention are known or they may be prepared by methods known in the art. The term alkali metals as used herein refers to the Group 1a metals lithium, sodium, potassium, rubidium, and cesium. The term alkaline earth metals refers to the Group 2a metals beryllium, magnesium, calcium, strontium, and barium.

The reaction according to Equation 1 is most conveniently carried out in an inert aprotic solvent, such as an aliphatic or an aromatic hydrocarbon or a halogenated aliphatic or aromatic hydrocarbon or mixtures thereof at or near the boiling point of the solvent. Preferred solvents are those which boil above 100° C., with those that boil above 130° C. being more preferred because reaction times are shorter. It will be recognized by those skilled in the art that solvents with boiling points below 100° C. may also be employed if the reaction is carried out under sufficient pressure to elevate the boiling point of the solvent to a temperature above 100° C.

According to the invention, the rate of reaction between the acid chloride and the phenol sulfonic acid salt can be accelerated by adding a phase transfer catalyst to the reaction medium. Suitable phase transfer catalysts can be selected from among those described by C. M. Starks and C. Liotta in "Phase Transfer Catalysis, Principles and Techniques" (Academic Press, Inc., N.Y., N.Y., 1978) and among those described by E. V. Dehmlow and S. S. Dehmlow in "Phase Transfer Catalysis, 2nd Ed." (Verlag Chemie GmbH, D-6940 Weinheim, 1983), the teachings of which are incorporated herein by reference. Quaternary ammonium and quaternary phosphonium salts are particularly useful phase transfer catalysts for practicing the process of this invention. Useful quaternary ammonium and phosphonium salts include, but are not limited to, chlorides, bromides, iodides, fluorides, hydrogen sulfates, sulfates and dihyrogen phosphates. The chloride salts are preferred for their high catalytic activity and because of a reduced likelihood of producing undesirable colored by-products. In addition, since residual amounts of the halide may persist in the final product, chlorides are preferred over bromides and iodides, because chloride is not as readily oxidized in wash water to a corresponding hypohalite, which, in turn, can cause fabric dye damage.

Any practical amount of catalyst may be employed to achieve the desired increase in the rate of reaction, preferably the amount of catalyst employed should be between about 0.1 and 10 mole percent relative to the amount of phenol derivative present in the reaction. In a preferred embodiment, the amount of catalyst employed should be from about 1 to 5 mole percent relative to the amount of phenol derivative present.

Specific phase transfer catalysts which can be used according to the improved process of this invention include, but are not limited to, tetramethylammonium bromide, tetramethylammonium chloride, tetramethylammonium hydrogen sulfate, tetramethylammonium sulfate, tetramethylammonium iodide, tetraethylammonium bromide, tetraethylammonium chloride, tetraethylammonium hydrogen sulfate, tetraethylammonium iodide, tetrapropylammonium bromide, tetrapropylammonium chloride, tetrapropylammonium hydrogen sulfate, tetrapropylammonium iodide; methyltriethylammonium bromide, methyltriethylammonium chloride, methyltriethylammonium hydrogen sulfate, methyltriethylammonium iodide, methyltripropylammonium bromide, methyltripropylammonium chloride, methyltripropylammonium hydrogen sulfate, methyltripropylammonium iodide, methyltributylammonium bromide, methyltributylammonium chloride, methyltributylammonium hydrogen sulfate, methyltributylammonium iodide, tetrabutylammonium fluoride, tetrabutylammonium dihydrogenphosphate, tetrabutylammonium bromide, tetrabutylammonium chloride, tetrabutylammonium hydrogen sulfate, methyltrioctylammonium bromide, methyltrioctylammonium chloride, methyltrioctylammonium iodide, octadecyltrimethylammonium bromide, Aliquat® 336, hexadecyltrimethylammonium bromide, hexadecyltrimethylammonium chloride, benzyltrimethylammonium bromide, benzyltrimethylammonium chloride, benzyltriethylammonium bromide, benzyltriethylammonium chloride, benzyltributylammonium bromide, benzyltributylammonium chloride, tetrabutylphosphonium bromide, tetrabutylphosphonium chloride, hexadecyltributylphosphonium bromide, tetraphenylphosphonium bromide, tetraphenylphosphonium chloride, methyltriphenylphosphonium bromide, and methyltriphenylphosphonium iodide.

The optimum solvent, catalyst and temperature for carrying out the process of this invention will depend on the nature of the phenol sulfonic acid salt (III) and the acid chloride or chloroformate (II) which comprise the starting materials. The order of addition of the starting materials is not critical; however, it is preferable to add the acid chloride or chloroformate (II), or a solution of it in the reaction solvent, to a stirred mixture of the phenol derivative (III) and the catalyst in the reaction solvent. Although it is not essential, it can be advantageous to carry out the reaction of Equation 1 under an atmosphere of an inert gas, such as argon or nitrogen.

In cases where the phenol derivative (III) is obtained as a hydrated material, it is beneficial to remove as much water as possible prior to the addition of the acid halide or chloroformate (II). This may be conveniently accomplished by drying the phenol derivative in a vacuum oven or by azeotropic removal of the water in the presence of an appropriate solvent. Thus, in such cases, a reaction solvent should be selected which permits the azeotropic removal of water prior to the addition of the acid halide or chloroformate (II). Examples of such solvents include aliphatic and aromatic hydrocarbons and halogenated aliphatic and aromatic hydrocarbons, the specific selection of which is within the knowledge of those skilled in the art.

The reaction according to Equation 1 may be carried out using any practical ratio of the starting materials (II) and (III). Best results are achieved, however, using a 1:1 molar ratio of the reactants or a small excess of the acid chloride, contrary to the teachings of the prior art. The use of a small excess, i.e., 20% or less, of the acid chloride or chloroformate (II) allows practically complete conversion of the phenol sulfonic acid salt (III) in a commercially feasible period of time.

In most cases the product of formula (I) will be insolvent in the reaction solvent at ambient temperature and will separate from it in pure form. Intermediates, which, because of their nature, are soluble in the reaction solvent, can be isolated by evaporation of the solvent or by precipitation from the reaction medium by the addition of a solvent in which the intermediate is of low solubility. Compounds of formula (I) may be further purified by recrystallization or trituration with water or organic solvents or mixtures thereof. Mixtures of water and alcohols, such as methanol, ethanol and isopropanol, are well suited to this purpose.

The compounds within the scope of formula (I) are useful as bleach activators and as additives for laundry detergents. The process of this invention is further illustrated in the following examples. As employed in the Examples, Aliquat ® 336 is trioctylmethylammonium chloride (mixture if $C_8$–$C_{10}$; $C_8$ dominant).

EXAMPLE 1

Preparation of 4-nonanoyloxybenzenesulfonio acid, sodium salt

Method A

A suspension of 98 g (0.49 mole) of vacuum dried (140° C., 18 hr) 98% 4-hydroxybenzenesulfonic acid, sodium salt, in 1 liter of mixed xylenes was heated to reflux for 2 hrs with azeotropic removal of a small amount (less than 1 ml) of water. To this mixture was then added 106 g (0.59 mole) of 98% nonanoyl chloride and 7.4 g (0.025 mol) of tetra-n-butylphosphonium chloride, and reflux continued for 5 hrs under nitrogen. On cooling, the suspended product was collected, washed with 200 ml of mixed xylenes and dried at 65° C. under reduced pressure to give 153 g of white solid. $^1$H NMR(DMSO-$d_6$, 300 MHz) of this material showed only absorptions expected for the product; δ 0.85 t, 3H, $CH_3$), 1.3 (m, 10H, $(CH_2)_5$), 1.65 (m, 2H, $CH_2$), 2.55 (t, 2H, $CH_2CO_2$), 7.05 (d, 2H), 7.7 (d, 2H). High pressure liquid chromatography (HPLC) of this material, using a Zorbax ® ODS column eluting over a gradient from 80% PICA ® (Waters):20% acetonitrile to 30% PICA ®: 70% acetonitrile indicated that it contained 91% of 4-nonanoyloxybenzenesulfonic acid, sodium salt and 2.3% 4-hydroxybenzenesulfonic acid, sodium salt. Based on this, the chemical yield was 84% from 4-hydroxybenzenesulfonic acid, sodium salt.

Method B

A suspension of 232 g (0.98 mole) of 98% 4-hydroxybenzenesulfonic acid, sodium salt, dihydrate, in 1 liter of mixed xylenes was heated to reflux for 5 hrs with azeatropic removal of water (33 ml). To this mixture was then added 16.2 g of ALIQUAT ® 336 and reflux continued for an additional 0.5 hr to remove a small amount (0.2 ml) of water. The temperature of the mixture was adjusted to 130° C. and 202 ml (1.10 mole) of 98% nonanoyl chloride was then added over 15 minutes and reflux then continued for 3 hrs under nitrogen. The mixture was then cooled to 90° C., the suspended product collected, washed twice with 200 ml portions of mixed xylenes and dried at 50° C. under reduced pressure to give 322.6 g of white solid. $^1$H NMR (DMSO-$d_6$, 300 MHz) of this material showed only absorptions expected for the product. HPLC indicated that it contained 97% of 4-nonanoyloxybenzenesulfonic acid, sodium salt, and 0.81% of 4-hydroxybenzenesulfonic acid, sodium salt. Based on this, the yield was 95% from 4-hydroxybenzenesulfonic acid, sodium salt.

EXAMPLE 2

Preparation of 4-decanoyloxybenzenesulfonic acid, sodium salt

The procedure and scale of Example 1 was followed using 114.4 g (0.6 mole) of decanoyl chloride to yield 162.1 g of white solid. $^1$H NMR(DMSO-$d_6$, 300 MHz) δ 0.85 (t, 3H, $CH_3$), 1.3 (m, 12H, $((CH_2)_6)$), 1.65 (m, 2H, $CH_2$), 2.55 (t, 2H, $CH_2CO_2$), 7.1 (d, 2H, 7.7 (d, 2H).

EXAMPLE 3

Preparation of 4-(octanoyloxyacetoxy)benzenesulfonic acid, sodium salt

A suspension of 58 g (0.25 mole) of 98% 4-hydroxybenezenesulfonic acid, sodium salt, dihydrate in 250 ml of mixed xylenes was heated to reflux for 6 hrs with azeotropic removal of water. To this mixture was then added 2.2 g (0.0075 mole) of tetra-n-butylphosphonium chloride, and azeotropic removal of water continued for 30 minutes. To the resulting mixture was then added 66 g (0.30 mole) of octanoyloxyacetyl chloride and the mixture was heated at reflux for 7.5 hours. The mixture was allowed to cool to 75° C., the product was collected by filtration, was washed with 100 ml of warm xylenes, and was dried under vacuum at 65° C. to give 86.6 g of white solid. $^1$H NMR(DMSO-$d_6$) of this material showed only absorptions expected for the product; δ 0.85 t, 3H, $CH_3$), 1.3 (m,10H, $(CH_2)_5$), 1.65 (m, 2H, $CH_2$), 2.4 (t, 2H, $CH_2CO_2$), 4.95 (s, 2H, $CO_2CH_2CO_2$), 7.1 d, 2H), 7.7 (d, 2H).

HPLC of this material using the system described in Example 1 indicated that it contained 77% 4-(octanoyloxyacetoxy)benzenesulfonic acid, sodium salt and 11% of 4-hydroxybenzenesulfonic acid, sodium salt. The indication in the NMR spectrum of a substantial absence of 4-hydroxybenesulfonic acid, sodium salt, would suggest that this product could degrade under the conditions of the HPLC analysis and that actual purity is much higher.

EXAMPLE 4

Preparation of 4-(nonanoyloxyacetoxy)benzenesulfonic acid, sodium salt

A suspension of 186 g (0.78 mole) of 98% 4-hydroxybenzenesulfonic acid, sodium salt, dihydrate, in 1 liter of mixed xylenes was heated to reflux for 15 hrs with azeotropic removal of water. To this mixture was then added 6 g (0.02 mole) of tetra-n-butylphosphonium chloride followed by the addition of 235 g (1.0 mole) of nonanoyloxyacetyl chloride over 15 minutes. The mixture was heated to reflux for 9 hrs and an additional 6 g (0.02 mole) of tetra-n-butylphosphonium chloride was then added. After an additional 3 hrs at reflux the mixture was allowed to cool, the product was collected by filtration, was washed thoroughly with petroleum ether, and was dried under vacuum at 90° C. to give 293 g of white solid.

HPLC of this material using the system described in Example 1 indicated that it contained greater than 95% 4-(nonanoyloxyacetoxy)benzenesulfonic acid, sodium salt. Based on this, the yield was 91% from 4-hydroxybenzenesulfonic acid, sodium salt.

EXAMPLE 5

Preparation of 4-(octylsulfonylacetoxy)benzenesulfonic acid, sodium salt

A suspension of 26.5 g (0.112 mole) of 98% 4-hydroxybenzenesulfonic acid, sodium salt, dihydrate, in 250 ml of mixed xylenes was heated to reflux for 8 hrs with azeotropic removal of water. To this mixture was then added 1.5 g (0.0005 mole) of tetra-n-butylphosphonium chloride followed by 37 g (0.144 mole) of octylsulfonylacetyl chloride and the mixture heated at reflux for 7 hrs. The mixture was cooled, the product was collected by filtration, was washed thoroughly with petroleum ether, and was dried under vacuum at 60° C. to give 46.1 g of light brown solid. $^1$H NMR(DMSO-d$_6$) of this material showed only absorptions expected for the product; δ 0.89 (t, 3H, CH$_3$), 1.3 (m, 8H, (CH$_2$)$_4$); 1.46 (m, 2H, CH$_2$), 1.87 (m, 2H, CH$_2$), 3.38 (t, 2H, CH$_2$SO$_2$), 4.66 (s, 2H, SO$_2$CH$_2$CO$_2$), 7.1 (d, 2H), 7.7 (d, 2H).

HPLC of this material using the system described in Example 1 indicated that it contained greater than 96% 4-(octylsulfonylacetoxy)benzenesulfonic acid, sodium salt. Based on this, the yield was 98% from 4-hydroxybenzenesulfonic acid, sodium salt.

Contemplated equivalents for the process of this invention are those cases in which the acid chloride (II) is derived from any carboxylic acid so long as the acid is free of functional groups which would interfere with the process. Also included in this group are diacid chlorides such as those derived from C$_6$-C$_{20}$ linear dicarbonylic acids. In the same way, the phenyl group of the starting hydroxybenzenesulfonic acid salt may be partially or fully substituted so long as the substituted group does not interfere with the process.

What is claimed is:

1. A process for preparing benzenesulfonate salts of the formula (I)

$$RCO_2PhSO_3M \quad (I)$$

where:
R is C$_5$-C$_9$ linear alkyl; CH$_2$So$_2$R$_3$; or CH$_2$OC(O)R$_6$
R$_3$ is C$_1$-C$_{14}$ alkyl;
R is C$_5$-C$_9$ linear alkyl; CH$_2$So$_2$R$_3$; or CH$_2$OC(O)R$_6$ M is selected from an alkali metal or an alkaline earth metal by reacting an acid chloride of the formula (II)

$$RCOCl \quad (II)$$

with a phenol sulfonic acid salt of the formula (III)

$$HOPhSO_3M \quad (III)$$

in an inert aprotic solvent having a boiling point above 100° C., the improvement comprising reacting said acid chloride with said phenol sulfonic acid salt in the presence of from 0.1 to 10 mole percent of a phase transfer catalyst selected from quaternary ammonium and quaternary phosphonium salts based on the amount of phenol sulfonic acid salt present in the reaction.

2. The process of claim 1 in which the phase transfer catalyst is a tetraalkylammonium salt and M is sodium.

3. The process of claim 1 in which the phase transfer catalyst is a tetraalkylphosphonium salt and M is sodium.

4. The process of claim 2 in which tetraalkylammonium salt is a chloride salt.

5. The process of claim 3 in which the tetraalkylphosphonium salt is a chloride salt.

6. The process of claim 1, claim 3 or claim 5 in which the acid chloride is nonanoyl chloride, the phenol sulfonic acid is 4-hydroxybenzenesulfonic acid, sodium salt, the phase transfer catalyst is tetra-n-butylphosphonium chloride, and the inert aprotic solvent is mixed xylenes.

7. The process of claim 1, claim 3 or claim 5 in which the acid chloride is octanoyloxyacetyl chloride on nonanoyloxyacetyl chloride, the phenol sulfonic acid is 4-hydroxybenzenesulfonic acid, sodium salt, the phase transfer catalyst is tetra-n-butylphosphonium chloride, and the inert aprotic solvent is mixed xylenes.

8. The process of claim 1, claim 2 or claim 4 in which the acid chloride is nonanoyl chloride, the phenol sulfonic acid is 4-hydroxybenzenesulfonic acid, sodium salt, the phase transfer catalyst is tetramethylammonium chloride, and the inert aprotic solvent is mixed xylenes.

9. The process of claim 1, claim 2 or claim 4 in which the acid chloride is nonanoyl chloride, the phenol sulfonic acid is 4-hydroxybenzenesulfonic acid, sodium salt, the phase transfer catalyst is trioctylmethylammonium chloride, and the inert aprotic solvent is mixed xylenes.

* * * * *